(12) United States Patent
Axelgaard et al.

(10) Patent No.: US 6,198,955 B1
(45) Date of Patent: Mar. 6, 2001

(54) MEDICAL ELECTRODE METHOD OF MANUFACTURE

(75) Inventors: Jens Axelgaard, Fallbrook; Steve Heard, Escondido, both of CA (US)

(73) Assignee: Axelgaard Manufacturing Co., LTD, Fallbrook, CA (US)

( * ) Notice: Subject to any disclaimer, the term of this patent is extended or adjusted under 35 U.S.C. 154(b) by 0 days.

(21) Appl. No.: 09/408,004

(22) Filed: Sep. 29, 1999

Related U.S. Application Data

(62) Division of application No. 09/021,009, filed on Feb. 9, 1998, now Pat. No. 6,038,464.

(51) Int. Cl.⁷ .................................................. A61B 5/04
(52) U.S. Cl. ..................... 600/391; 600/397; 156/292; 29/592.1; 29/825; 204/414; 252/519.33
(58) Field of Search ..................... 600/372, 386, 600/391–397; 603/32; 607/152, 149; 156/247, 292, 267, 268; 29/592.1, 825; 204/414; 252/519.33

(56) References Cited

U.S. PATENT DOCUMENTS

| | | | |
|---|---|---|---|
| 4,066,078 | * | 1/1978 | Berg ................................ 600/391 |
| 4,515,162 | * | 5/1985 | Yamamoto et al. ................. 128/640 |
| 5,069,908 | * | 12/1991 | Henley .............................. 424/449 |
| 5,330,516 | * | 7/1994 | Nathan ................................ 607/48 |
| 5,421,982 | * | 6/1995 | Ikeda et al. ........................ 56/226 |
| 5,674,275 | * | 10/1997 | Tang et al. ......................... 607/152 |
| 5,713,128 | * | 2/1998 | Schrenk et al. ..................... 29/885 |
| 5,868,136 | * | 2/1999 | Fox et al. .......................... 252/500 |

* cited by examiner

Primary Examiner—Linda C. M. Dvorak
Assistant Examiner—David M. Ruddy
(74) Attorney, Agent, or Firm—Walter A. Hackler

(57) ABSTRACT

An electrode provides electrical contact with a patient's skin with the electrode including a conductive member for connection to an external electrical apparatus and multilayers of gel for providing electrical interface between the patient's skin and the conductive member. A first layer is provided which includes an electrically conductive gel having a relatively low peel strength for removably contacting the patient's skin and a second layer is provided which includes an electrically conductive gel having a relatively high peel strength for contacting the conductive member. The first and second layers are laminated in accordance with the method of the invention. Other layers may be utilized in combination with the first and second layers. Such layers include a scrim layer and a layer including physiologically active ions. Further, the electrode through the use of multilayer gels is suitable for use with garments for the selective positioning of electrodes to a patient's skin.

10 Claims, 2 Drawing Sheets

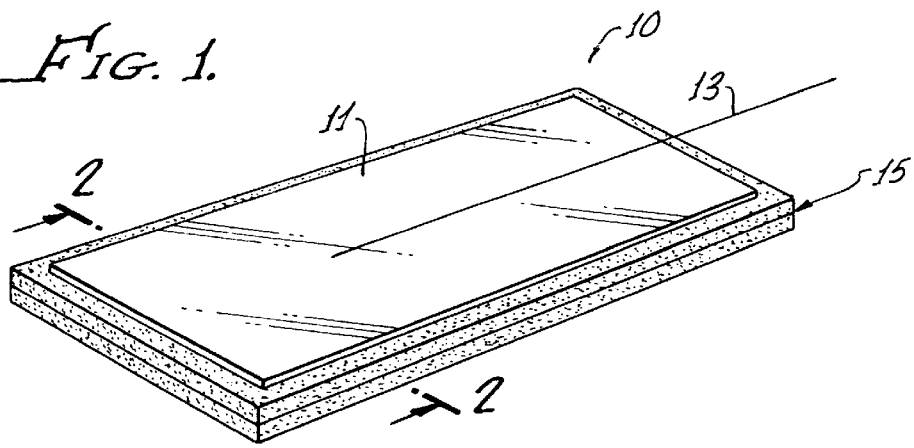
FIG. 1.
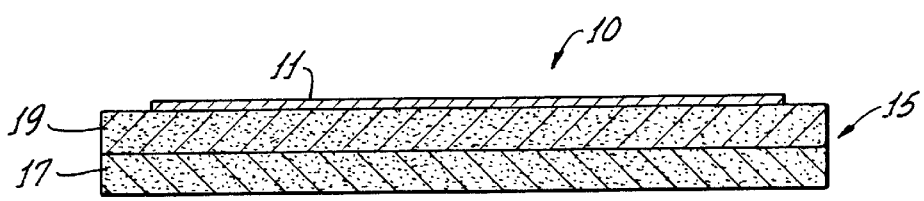
FIG. 2.
FIG. 3.
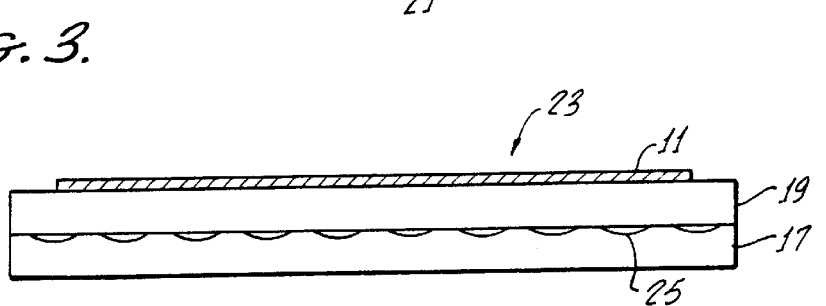
FIG. 4.
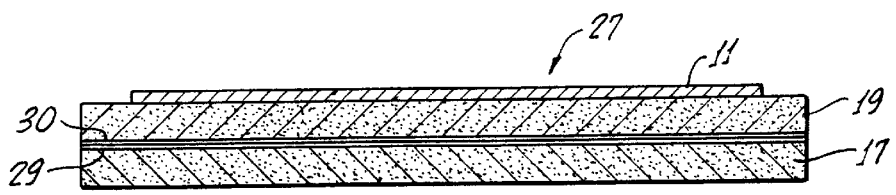
FIG. 5.

MEDICAL ELECTRODE METHOD OF MANUFACTURE

This application is a divisional of application Ser. No. 09/021,009, filed Feb. 9, 1998, now U.S. Pat. No. 6,038,464.

FIELD OF THE INVENTION

The present invention provides a combination electrode for use in medical applications, e.g., medical applications requiring monitoring, stimulation or iontophoresis, having an electrical current conductor including a connector in addition to a skin-interfacing film wherein this film may have adhesive, plastic and hydrophilic properties such as may reside in an electrically conductive, polymeric composition.

BACKGROUND OF THE ART

Medical electrodes have, in the past, taken many shapes and forms. Principally, they have been shaped according to the use for which they are intended. Electrodes used with monitoring apparatus, such as EKG and EEG machines, commonly have small round contact surfaces, whereas electrodes used with such stimulation apparatus as pain control devices tend to be larger and have rectangularly, circularly and other conveniently shaped contact surfaces. Whether intended for monitoring or stimulation use, a design objective for each electrode group has been, and continues to be, good electrical signal transmission between a patient's skin surface and the electrical cables connected to a particular piece of apparatus. With respect to stimulation and monitoring electrodes, efficient signal transmission across the epidermis conductor interface is desirable. Further, with respect to stimulation electrodes, effective signal transmission free of current concentration points or "hot spots" is also desirable.

Of the electrodes presently available, many offer combination structures including a metallic or otherwise conductive support member to which an electrical wire from an associated apparatus may be attached.

Certain of the currently available electrodes, including electrical stimulation electrodes are disclosed in U.S. Pat. Nos. 4,722,354; 4,736,752; 4,819,328; 5,038,796 and 5,450,845 to Axelgaard et al which are hereby incorporated by reference to show various electrode designs including but not limited to medical electrode shapes, structures, materials and means and methods for connecting said medical electrodes to the appropriate electrical apparatus.

In many instances, the medical electrodes of the prior art need the addition of generous amounts of an electrode paste or gel applied directly to the conductive support member to enhance conductivity across the skin-electrode interface to the point where acceptable operating conditions are achieved.

The prior art electrodes that require an electrode paste or gel or electrolyte solution provide a structure which does not always maintain constant, efficient and effective electrical transmission for long periods of time without the need for additional electrode paste, gel or solution. Moreover, there is a tendency while using these electrodes, for the electrode gel to separate and/or to flow to a non-uniform thickness. Under these conditions, sections of the conductive support member could be exposed to the skin and local hot spots can result which can cause discomfort if not severe enough to cause burns to the patient's skin. Therefore, medical electrodes wherein the adhesive, itself, provides the conductive interface between the skin and the electrical connector are very desirable. An electrode of this type is disclosed in U.S. Pat. No. 4,066,078 to Berg. In this patent, the polymer itself acts as the adhesive and, through the quaternary groups attached to the polymer backbone, provides a conductive interface.

Nevertheless, others have continued to formulate adhesive materials that effectively adhere to the skin. For example, materials that can be utilized in fabricating a medical electrode and also provide adequate conductivity are referenced in U.S. Pat. Nos. 4,830,776; 4,274,420; 4,777,954; 4,699,146; 4,458,696; 5,024,227; 4,243,051.

Copending U.S. patent application Ser. No. 08/603,635, now U.S. Pat. No. 5,868,136, provides an electrode with an improved electro-conductive skin-interface substrate, which will perform a similar function to, and eliminate the need for, an electrolyte solution, electrode paste or electrode gel. This patent is to be totally incorporated by this reference to show suitable materials useful in the present invention. However, conductive adhesives and/or gels heretofore developed offer compromise properties such as, for example, peel strength which may be suitable for permanent adhesion to a conductive member but accordingly do not offer or facilitate repeated removal and contact with a patient's skin.

In addition, heretofore manufacture of conductive gel electrodes has included separate handling of the gel before application to a conductive member. Because of the poor strength of the gels, a scrim is often embedded into the gel in order to enable handling of the gel and its application to a surface of a conductive member. If a scrim is not used, the gel may stretch or distort during handling which results in an uneven layer of gel or the conductive member. This results in poor and/or unreliable current densities provided by the electrode.

However, the use of a scrim in prior art electrodes introduces yet another problem. That problem is accurate placement of the scrim within the gel. Currently, a scrim is introduced into the gel upon extrusion of the gel into a layer. In this procedure accurate placement within the gel layer has proved to be very difficult since the scrim tends to float or sink within the gel before curing or setting thereof.

It should be appreciated that if the scrim ends up too close to the gel surface facing the conductor, delamination occurs and if the scrim ends up too close to the gel surface contacting a patient's skin, causes inadequate adhesion, often resulting in partial or full separation of the electrode from the skin.

In accordance with the present invention, an electrode is provided with a multilayer substrate that has very good skin characteristics such as softness, wetness and readhesion, while at the same time having excellent permanent adhesion to a conductive member.

In addition, when a scrim is desirable, the method of the present invention enables accurate placement thereof within the multilayer gel so as to eliminate all prior problems, hereinabove discussed, with regard to the use of such scrims. A further feature of the present invention includes the structure enabling accurate incorporation of a physiologically active agent or ions, for iontophoresis in a more economical and efficacious way than the prior art.

Yet, another feature of the present invention is the use of conductive layers having widely different adhesivity or specificity to widely different substrates. As will be set forth herein, this enables an electrode to be used in combination with a garment in which the electrode slides over a patient's skin.

Other objects and advantages of the present invention will become apparent from a careful reading of the specification below.

SUMMARY OF THE INVENTION

An electrode in accordance with the present invention, suitable for stimulation, monitoring and drug delivery applications, generally includes a conductive member, or substrate, including means for providing electrical connection to an external electrical apparatus. A conductive member may be any suitable type of film or fabric as may be, for example, described in the hereinabove referenced U.S. patents.

In addition, the electrode includes a multi-layered structure which provides a means for providing electrical interface between a patient's skin and the conductive member, the multi-layered structure being adhered to the conductive member.

More particularly, the multi-layer includes a first layer which includes an electricaly conductive gel having a relatively low peel strength which provides a means for removably contacting the patient's skin. The first, or skin contact layer in accordance with the present invention, may be soft, with a wet feeling and have an affinity for skin adhesion while at the same time enabling easy separation, or peeling from the skin. In addition, a second layer is provided which includes an electrically conductive gel having a relatively high peel strength is provided for contacting the conductive member. The second, or substrate contact, layer may be more firm than the first layer, but importantly, have an affinity for permanent adhesion to the substrate.

The relatively low peel strength characteristics of the first layer, as will be hereinafter described in greater length, provides for easy reusable attachment to a patient's skin, while the second layer is a very high and substrate specific adhesitivity and accordingly, forms a permanent bond with the conductive layer.

The first and second layers are laminated to provide a unitary structure exhibiting both ideal properties for reattachment to a patient's skin and permanent attachment to the conductive member. Both the first and second layers preferably have viscoelastic conductive, adhesive and hydrophilic properties which comprises an electrically conductive organic polymer plasticized with a polyhydric alcohol, for example, glycerol, propylene glycol, polyethylene glycol and polypropylene glycol, among others.

The distinct separate properties of each of the layers of the multilayered electrode in accordance with the present invention may be achieved by utilizing different amounts of plasticizers in the first and second layers, which are laminated by curing.

More particularly, the electrode in accordance with the present invention may include an inorganic polymer derived from a monomeric mixture comprising from about 12 to about 30 pph acrylic acid, about 0.5 to about 30 pph N-vinylpyrrolidone and about 0.01 to about 2 pph of a crosslinking agent and from about 0.5 to about 8 pph of a thickening agent comprising a N-vinylpyrrolidone/acrylic acid copolymer.

To tailor the differing characteristics of the first and second layer, the first layer may comprise more glycerol than the second layer. In addition, the first layer may comprise less N-vinylpyrrolidone than the second layer.

Still further tailoring of the different characteristics of the first and second layers may be accomplished by utilizing a different cross-linking agent in each of the first and second layers. Preferably, the amount of monomeric mixture in both of the first and second layers includes an ultraviolet sensitive curing agent, which again may be different in each layer to effect the necessary divergent properties of the layers within the electrode in accordance with the present invention.

Still more particularly, the electrode in accordance with the present invention may include a scrim disposed between the first and second layers and laminated therebetween in order to modify or control the physical characteristics of the combined first and second layer.

The scrim may be a fabric or screen material. However, and in accordance with the present invention, the scrim may, in fact, be another curable conductive gel layer as will be discussed in greater detail hereinafter. This scrim layer may include reinforcement fibers or particulates such as, for example, cellulose or silica as well as any suitable natural or sythetic fibers and other mineral particulates.

In addition, for the purpose of iontophoresis, physiologically active ions may be provided between the first and second layers and laminated therebetween. These ions may be included as a third layer between the first and second layers or disposed in pockets formed in one of the first and second layers.

When a layer including physiologically active ions is included, the scrim layer, hereinabove noted, may also be used as a barrier in order to prevent reverse diffusion of the ions into the second layer.

In another embodiment of the present invention, the adhesivity of the first layer is controlled in order to enable the electrode to be slidably disposed against the patient's skin. In this embodiment the conductive member is attached to a garment by yet another layer of adhesive. The adhesivity of each of the layers is controlled to enable different adhesion. That is, the first layer can be removed from the skin without separation of the conductive member and the garment and the conductive member can be removed from the garment without separating the second layer from the conductive member.

A method in accordance with the present invention for making an electrode generally includes the steps of disposing a first layer of an electrically conductive first curable liquid onto a film, with a first layer upon curing of the first liquid, having a relatively low peel strength to enable removal from the film and subsequent removable contact with a patient's skin. Following this disposition, the first liquid is partially cured and thereafter a second layer of an electrically conductive second curable liquid is disposed onto the partially cured first liquid, with the second layer upon curing of the second liquid, having a relatively high peel strength to enable permanent contact with a conductive member.

Thereafter, the partially cured first layer and the second layer are cured to form a laminate and a conductive member is permanently disposed upon the cured second liquid.

It should be appreciated that the hereinabove described method of partially curing may be reversed. That is, the second layer may be formed and partially cured with subsequent applications of the first layer and a total curing of both the first and second layers.

Suitable electrically conductive organic polymers useful in the adhesive composition utilized in the medical electrode of the present invention include copolymers derived from the polymerization of acrylic acid and N-vinylpyrrolidone. Such copolymer may further include the following comonomers: acrylamide, 2-acrylamido propane sulfonic acid and methylene-bis-acrylamide.

The adhesive composition may also include a thickener such as a copolymer of ethylene and maleic anhydride, or methylvinylether and maleic anhydride, or N-vinylpyrrolidone and acrylic acid, or polyacrylic acid, polyvinyl alcohol, polyvinylacetate or gelatin.

The precursor to said adhesive composition is copolymerized to yield a film having suitable adhesive properties and electroconductivity properties for use as a medical electrode adhesive in the presence of an ultraviolet sensitive curing agent such as 2-hydroxy-2-methyl-1-phenyl-propan-2-one (available as Darocur 1173®), 4-(2-hydroxyethoxy)-phenyl-(2-hydroxy-2-phenyl-(2-hydroxy-2-propyl)ketone (available as Darocur 2959®), or 2,2-dimethoxy-2-phenylacetophenone (available as Irgacure® 651). The Darocur 2959® curing agent is most active at about 308 nm UV light which enables curing with a UV light source having a peak frequency at about 308 nm in order to reduce overall heating of the layers during curing as will be hereinafter discussed.

BRIEF DESCRIPTION OF THE DRAWINGS

The advantages and features of the present invention will be better understood by the following description when considered in conjunction with the accompanying drawings in which:

FIG. 1 is a perspective view of the electrode;

FIG. 2 is a cross-section in side elevation through the electrode of FIG. 1 taken along the line 2—2 showing a multilayer interface;

FIG. 3 is a cross section of an alternative embodiment of the present invention showing a scrim disposed between layers of gel;

FIG. 4 is a cross section of another alternative embodiment of the present invention showing pockets of a physiologically active ion disposed between layers of gel;

FIG. 5 is a cross section of yet another embodiment of the present invention showing a layer of a physiologically active ion disposed between layers of gel;

DETAILED DESCRIPTION OF THE INVENTION

Figure 6:
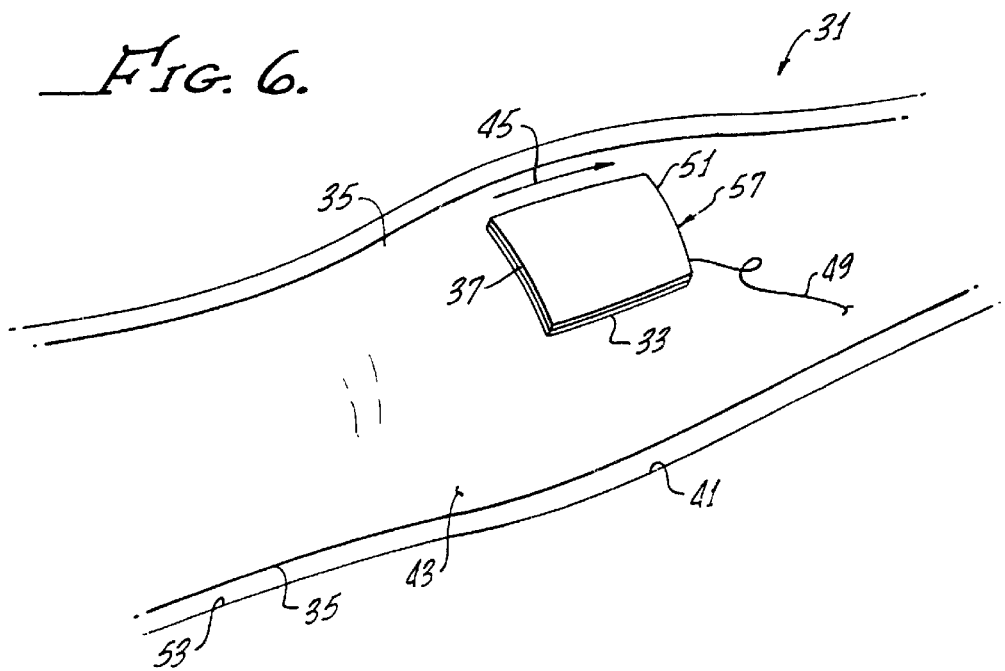
FIG. 6 is still another embodiment of the present invention in which the electrode includes a garment attached thereto and an exposed layer of the multilayer interface has an adhesivity enabling sliding movement along a patient's skin so that the electrode garment may be easily disposed and arranged on a patient's skin.

Medical electrodes are intended for usage as efficient and effective transmission mediums between a patient's skin and an electro-medical apparatus. Primary to their operation is a uniform conductivity through the electrode itself and a uniform conductivity across the electrode skin-interface. Uniform conductivity through an electrode is most often interrupted by a non-uniformity in the electrode materials. This may be due to a separation of some or all of the electrode interfacing material in contact with a patient's skin.

Preferably, the electrode is intended to be disposable; however, multiple use of the electrode on a patient's skin is often most preferable before disposal of the electrode. It is also important that the electrode have adhesive properties sufficient to be self-adhering to a patient's skin for approximately 8–12 hours. However, the electrode should contain sufficient flexibility and elasticity to move as a patient's skin moves while returning to original shape when permitted.

Additionally, it is very desirable to provide uniform conductivity with even current densities of approximately 30 microamperes per square millimeter when subjected to a stimulus of about 60 milliamperes at 35 cycles per second having pulse duration of about 250 microseconds. Additionally, it is important that an electrode be easily handled and non-irritating to a patient's skin. In some instances it is preferred that the electrode be sterilizable.

The electrode 10 configuration, in accordance with the present invention, is shown in FIG. 1 and, in cross section, in FIG. 2. Generally, a conductive member 11 is cut, stamped or otherwise shaped out of a piece of conductive material which may be aluminum foil or a conductive polymer coated with aluminum or tin. The shape to which this conductive member 11 is formed will depend upon the particular application in which it is to be used. Any suitable electrode 10 shape may be used and is sometimes round but may be as shown in FIG. 1, rectangularly shaped.

Alternately, other metallic foils, conductive polymers, graphitized or metalized cloth or wire mesh may be used as the conductive member. In particular, the knit conductive fabric disclosed in U.S. Pat. No. 4,722,354 may be utilized as the conductive member. For each material, an appropriate strength and thickness is to be chosen to yield a pliable, yet sufficiently strong member 11. When the conductive member 11 is of aluminum or tin foil, it usually is of 1–10 mil thickness.

Secured to the conductive member 11 is a connector 13 for providing a medium to which external signal cables may be attached for electrically communicating with the conductive member 11. This connector 13 may be a conductive swaged snap fastener, not shown in the accompanying drawings, which is available commercially. This fastener 13 is mechanically and electrically attached to the conductive member 11, in any suitable fashion. Preferably, the electrical connector 13 may be stranded stainless steel as shown in U.S. Pat. No. 4,722,359.

Abutting the inner surface of the conductive member 11 is an electrically conductive skin-interface substrate 15. This substrate 15 is multilayered for providing electrical interface between the patient's skin (not shown) and said conductive member 11. The multilayer 15 means includes first layer means 17, comprising an electrically conductive gel having a relatively low peel strength, for removably contacting the patient's skin (not shown) and second layer means 19, comprising an electrically conductive gel having a relatively high peel strength, for contacting said conductive member 11, the first and second layers 17, 19 being laminated. In general, the first and second layer means 17, 19 may comprise a curable liquid and the layers are laminated by curing.

It should be appreciated that the present invention is described herein, for the sake of clarity, as comprising two layers 17, 19, however, not limited thereto. In fact, any number of layers may be utilized in order to not only tailor the adhesive properties of exposed surfaces but to control integral strength of the multilayer means 15 as well as other significant properties such as current density provided by the electrode 10.

Referring again to FIG. 1, conductive substrate 15 is shaped correspondingly to the conductive member 11. When constructed in combination with a rectangular member 11, the substrate 15 is also rectangular. For TENS, FES, etc., electrodes 10, the first layer 17 may be relatively thick, for example, from about 10 mils to about 100 mils. The first layer which is a gel modified for skin affinity is backed with a relatively thinner second layer 19 which may be, for example, from about 1 mil to about 25 mils. This second layer 19 gel is modified for substrate adhesion and support. This configuration has been found to be particularly advantageous when supported internally by a thin open mesh scrim 21 (see FIG. 3) made of non-woven polyester. Other materials such as woven or non-woven polyester, nylon or polypropylene can also be used, as can cast or extruded sheets of polyethylene, etc., with holes or patterns punched through the material.

The supporting scrim 21, FIG. 3 may be used in electrode configurations where a greater thickness multilayer substrate 15 film is used. This scrim 21, while not a necessary part of the electrode, will tend to support by being distributed throughout the multilayer substrate 15. A further advantage to the use of this scrim 21 is that it acts to reenforce and strengthen the multilayer substrate 15.

The scrim 21 may be positioned between the layers 17, 19, in alignment with the conductive member 11, and is of a size to extend completely under the conductive member 11. Importantly, in accordance with the method of the present invention, the first layer 17 is partially cured before application of the second layer 19 and scrim, as will be discussed hereinafter in greater detail. The partial curing of the first layer 17 provides sufficient rigidity thereto to enable exact placement of the scrim 21 between the layers 17, 19. In fact, the scrim 21 may be selectively embedded into the first layer 17 as shown in FIG. 3 in order to control its structural effectiveness within the multilayer substrate 15.

The layers 17, 19 may be sheets or films of an electrically conductive organic polymer plasticized with a polyhydric alcohol, preferably glycerol.

As hereinabove noted, the scrim 21 may also be a curable liquid or film of the same type as that of the first and second layers 17, 19, but with a different curing agent, and/or photoinitiator such as, for example, Irgacure® and diethylene glycol diacrylate.

In addition to further stabilizing the structure, the scrim layer may include reinforcement fibers or particulates such as, for example, cellulose, silica, talc, among others. Applications and curing of the scrim layer will be hereinafter discussed in greater detail.

In general, the electrically conductive organic polymers that may be utilized in preparing the layers 17, 19 are derived from the copolymerization of a mixture of monomeric acrylic acid and N-vinyl-pyrrolidone. These polymers are set forth in U.S. patent application Ser. No. 08/603,635, now U.S. Pat. No. 5,868,136, which is incorporated herewith in toto to describe generally suitable polymers. For example, in general layers 17, 19, the organic polymer may comprise 25 to 75 parts per hundred, by weight (pph), e.g., 30 to 60 pph, acrylic acid and 2 to 30 pph, e.g. 10 to 30 pph, N-vinylpyrrolidone. In addition, the above mixture of comonomers, the organic polymer, may further include additional comonomers; in particular, 1 to 20 pph, e.g., 1 to 8 pph, acrylamide is desirable.

Furthermore, the organic polymer may comprise, e.g., 0.1 to 5 pph, e.g., about 2 pph, of a sulfonic acid-containing comonomer to (promote adhesion of the substrate), such as 2-acrylamide propane sulfonic acid (AMPS) and from, e.g., 0.1 to 5 pph, e.g., about 0.5 to 1.5 pph of a cross-linking agent, such as methyl-ene-bis-acrylamide, to increase to molecular weight and cohesivity of the conductive organic polymer through crosslinking. Other comonomers having at least two copolymerizable olefinic moeities, especially difunctional derivatives of acrylic acids, may be utilized in place of the preferred methylene bis-acrylamide, for example, tripropylene bis-methacylate, and diethylene glycol diacrylate.

The comonomer mixture may include both methylene-bis-acrylamide and acrylamide.

The comonomer mixture that is copolymerized to provide the organic polymer may also include a polyhydric alcohol, e.g., polyhydroxyhydrocarbons and oxyalkyls, e.g., ethyleneglycol, diethyleneglycol, glycerol, etc. to plasticize the organic polymer. The polyhydric functions as a humectant, i.e., it absorbs moisture and promotes conductivity of the substrate 15. The polyhydric alcohol may comprise from 25 to 75 pph, preferably from 40 to 60 pph, e.g., about 37 to 53 pph of the comonomer mixture. Most preferably, the polyhydric alcohol is glycerol.

The comonomer mixture that is copolymerized to provide the conductive organic polymer may also include a thickening agent. The thickening agent may be a high molecular weight polymer or copolymer such as a methylvinylether/maleic acid copolymer (Gantrez® S95), which is available from ISP, ethylene/maleic anhydride (EMA Copolymer), which is available from Zeeland Chemical, and N-vinylpyrrolidone/acrylic acid Acrylidone® (ACP-1041), which is available from ISP, 0.5 to 8 pph of the comonomer mixture, e.g., about 2 to 5 pph.

The above comonomer mixture is preferably copolymerized or cured by thermal chemical redox or radiation, particularly, ultraviolet (UV) radiation. Therefore, an ultraviolet sensitive curing agent is provided in the comonomer mixture at a concentration of from 0.05 to 3 pph, preferably from 0.5 to 2.0 pph. Suitable curing agents are 2-hydroxy-2-methyl-1-phenyl-propan-2-one (available as Darocur 1173®), 4-(2-hydroxyethoxy)phenyl (2-hydroxy-2-phenyl-(2-hydroxy-2-propyl)ketone (available as Darocur 2959®), or 2,2-dimethoxy-2-phenyl acetophenone (available as Irgacure® 651), all of which are available from Ciba-Geigy.

It is to be appreciated that the general formulations hereinabove described, while suitable as a conductive electrode adhesive, do not totally meet the requirements for optimum electrode use. As an example, for conductive members 11 which are difficult to adhere to substrates such as Polyvinyl Chloride, Polyolefin, polycarbonate, gels formulated as a single layer for both skin affinity and substrate adhesion have poor or inadequate adhesion.

It should be appreciated that the peel strength of the first layer 17 contacting the skin should be relatively low (i.e., up to about 100 grams cm) in order to provide adequate release of the electrode 10 from the skin whereas the second layer should have relatively high peel strength (i.e. over about 250 grams cm) in order to insure permanent contact with the conductive member.

Peel strength as used herein is defined as the amount of force necessary to peel a 2.5 cm strip of gel at 180° from a surface at the rate of 30 cm per min.

It has been found in accordance with the present invention that the first layer 17, improved skin adhesion occurs when the acrylic acid component is in the 10 to 15% range. For the second layer 19, improved conductive member 11 adhesion occurs when the acrylic acid component is in the high end of the range (20 to 30%). In order for the skin side adhesion to the first layer 17 to be non-"tape-like" or non-stringy (both undesirable for removal or repositioning of gel), water and plasticizer (glycerin, PEG, etc.) have to be high. However, for second layer 19, conductive member 11 adhesion without creep or crawl, the plasticizer and water must be low.

In addition, it has been unexpectedly found that the choice of crosslinking monomer and initiator both result in dramatically differing physical attributes to an otherwise similar gel formula. For example, monomers in the polyethylene glycol or polypropylene glycol diacrylate family (i.e., with polyethylene glycol or polypropylene glycol groups between the acrylic groups) contribute to high adhesion and cure rates but lack skin-wise preferable traits such as wetness and respositionability.

Accordingly, these crosslinking monomers are desirable for use in the second substrate adhesion layer 19.

Likewise, for the first layer 17, the polyethylene or polypropylene glycol dimethacrylate family have been found to contribute softness, wetness, non-tape like peel, non-stringy peel and excellent repositionability. In particular, a combination of diethylene glycol diacrylate in the substrate adherent gel layer and tripropylene glycol bis-methacrylate in the skin or first layer 17 has been found to be extremely effective in providing a high performance substrate adherent layer on the different substrates listed above but have outstanding skin side attributes including non-stringy peel and multiple repositionability.

Table 1 provides gellable comonomer mixtures optimized for first and second layers 17, 19 as well as a broad range of ingredients from which they are derived.

TABLE 1

| Ingredient | Broad Range pph | First Layer pph | Second Layer pph |
|---|---|---|---|
| acrylic acid* | 15–30 | 12.5 | 22 |
| n-Vinylpyrrolidone | 0.5–15 | 6 | 12.5 |
| acrylamide | 0–10 | 1.5 | 6 |
| methylene-bis-acrylamide | 0.01–2 | .18 | .12 |
| AMPS | 0.1–6 | 2.5 | 0 |
| thickener | 0.5–8 | 2.5 | 1.0 |
| glycerin | 25–75 | 48 | 40 |
| UV sensitive curing agent | 0.05–3 | .13(2959) | .20(1173) |
| distilled water | 5–25 | 26.7 | 18.2 |

Turning now to FIG. 4, there is shown an alternative embodiment 23 of the present invention which includes the conductive member 11 and first and second layers 17, 19 as hereinabove described, further including pockets 25 from between the first and second layers 17, 19 which includes the physiologically active compound, preferably an ionic form so as to enable iontophoresis into a patient's skin by application of current across the electrode.

Numerous ions have been utilized in iontophoresis such as local anesthetics. Any suitable ion may be useful such as, for example, Lidocaine®. In addition, iontophoresis may be utilized in edema reduction or to treat inflammatory conditions for example by using Decadron®. Other numerous skin conditions including idiopathetic hyperhidrosis, ulcers, and fungus infections may also be treated through the use of electrodes.

Turning to FIG. 4, the pockets are formed may be made in partially gelled first layer 17, as will hereinafter be described in greater detail.

Turning to FIG. 5, there is shown yet another electrode 27 in accordance with the present invention utilizing the conductive member 11 and first and second layers 17, 19 but with a layer 29 of physiologically active ions disposed therebetween. The principle operation being the same as that set forth and described in connection with the description of FIG. 4.

While the invention has hereinabove been described in connection with a first and second layer 17, 19, any number of layers may be utilized, as hereinabove noted, for various purposes, for example, as in FIG. 5, the layer 29 of physiologically active ions. Other layers of gel may be utilized to further tailor the electrical conductivity of the electrode. For example, as hereinabove noted, a scrim 30 may be disposed as a curable liquid and thereafter cured.

Importantly, the use of multilayers allows the electrode to be "tailored" for its end use. That is, the peel strength of the first layer may be varied depending upon the use of the electrode on the face, for cosmetic purposes, or other portions of the body.

Turning now to FIG. 6, there is shown yet another embodiment 31 in accordance with the present invention in which a first layer 33 is configured to enable sliding contact with a patient's skin 35. The formulation for this layer 33 may be as follows:

| Ingredients | PPH |
|---|---|
| Hydroxyethyl acrylate | 20 |
| N-vinylpyrrolidone | 5 |
| Diethylene glycol diacrylate | 0.5 |
| Glycerine | 45 |
| Irgacure 651 | 0.25 |
| Gelatin | 3.00 |
| DI water | 25 |
| Sodium Chloride | 1.25 |

The second layer 37 may have a formulation as hereinabove set forth for layer 19.

Figure 7:
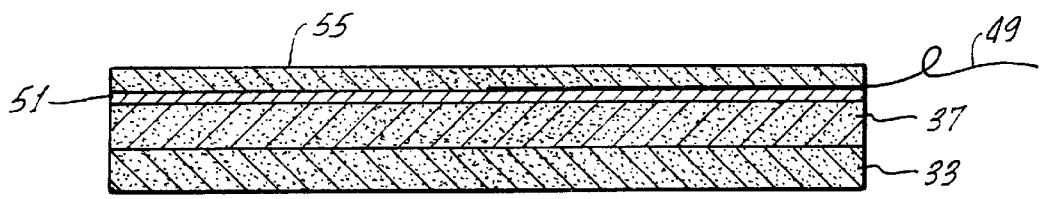
FIG. 7 is a cross sectional view of the electrode shown in FIG. 6.

This embodiment 31 includes a garment, such as for example, a sleeve 41 shaped as sized for disposal over a patient's arm 43, by sliding movement as shown by the arrow 45. An electrical lead wire 49, (see FIG. 7) attached to a conductive member 51, provides a means for connection to an external electrical apparatus (not shown).

Importantly, the conductive member 51 is removably attached to an inside surface 53 of the garment 41 by yet another adhesive layer 55 (See FIG. 7) and this enables the garment 41 to position the electrode 57 in a desired position on the patient's arm 43. Temporary pressure may be applied by the user to affix the first layer 17 to the patient's skin 35 with the garment 41 maintaining the position thereof. Further advantages of electrode pads for use on garments are set forth in U.S. Pat. Nos. 5,263,481 and 5,450,845 which are incorporated herein by this specific reference thereto.

In this embodiment 31, it is important to recognize that the structure of the multilayers 37, 39 enables differential release. That is, the first layer may have little or perhaps no tackiness or adhesion to the patient's skin 35, the second layer provides removable attachment to the conductive member 51 and a third layer 55 enables removal adhesion of the electrode 57 to the garment sleeve 41.

A method, in accordance with the present invention, of applying, or disposing, the first and second layers 17, 19 onto a conductive member 11, or film, is important in providing adhesion between the first layer 17 and the second layer 19. Hydrogels which are crosslinked to harden to an extent required for adhesion adequate for use in an electrode cannot be later laminated to another hydrogel. Such laminated gels will fail adhesively at the gel to gel interface. The present invention of casting and curing gel layers sequentially with partial curing provides for gel to gel interface exceeding that of the peel strength between the second gel and the conductive member.

First, in accordance with the present invention, a first layer 17 of hydrogel is laid down, or deposited, onto a film in any suitable method for example by roller application, gravure, extrusion, spraying, dipping, among others. As hereinabove noted, the hydrogel layers 17, 19 may be cured, or set, by UV radiation, electron beam, chemical redox or heat. The first layer 17 of liquid hydrogel may be coated in a layer from about 10 to about 100 mils thick on a silicon release film (not shown). A support mesh, or scrim, of non-woven polyester may be placed on top of the gel and the sandwich is then passed under an ultraviolet light to partially cure the first layer. The second layer 19 of curable hydrogel is then coated on top of the first layer at a thickness from about between one to 25 mils thick.

The completed sandwich is then exposed to ultraviolet light until both layers of gel are cured. This gel structure can then be covered by a silicone release treated cover until further processing or directly laminated to another substrate or applied to the conductive member 11.

By allowing the first coated layer 17 of the gel 20 partially cure at the first exposure, UV light induced chemical bonding between monomers of the hydrogels forms a final gel to gel adhesion interface. This interface is extremely strong and in fact exceeds the cohesive force of the individual gels.

When physiologically active ions are to be incorporated, pockets in the partially cured first layer 17 may be formed by depressing the surface of the partially cured first layer 17 with any suitable form (not shown). Thereafter, the physiologically active ions are disposed in the pockets before application of the second layer and final curing of both layers.

Alternatively, the physiologically active ions may be incorporated into a third hydrogel layer 29 which is applied to the partially cured first layer 17 with or without the scrim 21 before placement of the second layer 19 and first curing.

Further, it should be appreciated that, in accordance with the present invention, the formation of the first and second layers 17, 19 and the partial/full curing thereof may be reversed. The hereinabove description of the formation and curing of layers 17, 19 being only exemplary.

This reversal of the formation and curing of the layers teach to further advantage of the present invention. If the second layer 19 is first applied to the conductive member 11, with subsequent application of the first layer, no separate handling of the multilayer substrate 15 is required. That is, if the multilayer substrate 15 is directly formed on the conductive member, no procedures or separate step is required to apply a formed substrate 15 to the conductive member 11.

Thus, if the scrim 21 is not utilized to tailor other characteristics of the multilayer substrate 15, it can be eliminated. This leads to far thinner layers 17, 19 than possible with the scrim 21. The scrim 21, which may be a non-woven mesh, is typically 5 mil in thickness. Because of the problems hereinabove noted in the discussion of inaccuracy of scrim placement, thicker layers 17, 19 must be used when a scrim 21 is disposed between the layers 17, 19.

Without a scrim 21, the layers 17, 19 can be as thin as 10 mils. This structure further enhances the overall conductivity of the multilayer substrate 15. In this instance the second layer may be much thicker than the first layer 17 but with far greater conductivity. Hence, because the first layer 17 can be relatively thin, its conductivity does not reduce the total conductivity of the multilayer substrate 15, and, as a result, can be formed from a gel material offering even greater skin compatability.

When a liquid scrim 30 is utilized it may be applied as in accordance with the layers 17, 19 and thereafter cured. The scrim layer 30 may be used to strengthen the multilayer substrate 15 for subsequent handling thereof or, when the physiologically active ion layer 29 is utilized, it can provide a barrier for reverse diffusion of ions into the second layer 19. The scrim layer 30 is preferably conductive and comprised of the material hereinbefore set forth.

Another important aspect of the method of the present invention is to limit undesirable overheating of the conductive member 11 particularly when the member 11 is a carbon loaded film which may absorb considerable energy when a UV lamp is used for curing.

This is accomplished by using a photo initiator such as Darocur 2959®, which has a sensitivity to a particular UV wavelength.

Thus, UV radiation at or about that frequency can efficiently cure or set the resins in both the first step of partially curing the first layer and the second step of curing the first and second layers together without undue heating of the conductive member 11.

In this regard, the curing of the first and second layers 17, 19 may be considered a "cold" curing because little heating of the member 11 occurs. If standard broadband UV is used for curing, a carbon loaded conductive member 11 may be damaged, or at worst, vaporized. Significant protection of a carbon film conductive member 11 can also be achieved by applying the second layer first to the member 11 and thereafter partially curing the second layer 19 before application of the first layer 17 and final curing. In this manner the partially cured second first layer 17 provides a "shield" for the layer 19 and carbon film member 11.

In fact, all the layers 17, 19, 29, 30 hereinabove may each include different photoinitiation having highest curing efficient at different UV wavelengths. Then, the use of different UV lamps having maximum output at different UV wavelengths can more efficiently and selectively cure the various layers 17, 19, 29, 30 without undue heating. Such selective curing occurs in the multilayer structure because each layer can be cured by use of a different UV lamp or a plurality of UV lamps with different wavelength filters.

Although there has been hereinabove described an electrode with multilayer gel and method of manufacture in accordance with the present invention for the purpose of illustrating the manner in which the invention may be used to advantage, it should be appreciated that the invention is not limited thereto. Accordingly, any and all modifications, variations, or equivalent arrangements which may occur to those skilled in the art should be considered to be within the scope of the invention as defined in the appended claims.

What is claimed is:

1. A method of making an electrode, said method comprising the steps of:

disposing a first layer of an electrically conductive first curable liquid onto a film, said first layer upon curing of the first liquid having a relatively low peel strength to enable removal of said film and removable contact with a patient's skin;

partially curing the first liquid;

disposing a second layer of an electrically conductive second curable liquid onto said partially cured first liquid, said second layer upon curing of the second liquid having a relatively high peel strength to enable permanent contact with a conductive member;

curing the partially cured first liquid and second liquid to form a laminate;

disposing a conductive member on the cured second liquid.

2. The method according to claim 1 wherein the step of disposing the first layer comprises disposing an electrically conductive organic polymer with an amount of plasticizer and the step of disposing the second layer comprises disposing the same electrically conductive organic polymer with a lesser amount of plasticizer.

3. The method according to claim 2 wherein the step of disposing the first layer comprises disposing on the polymer a monomeric mixture comprising from about 15 to 30 pph acrylic acid, 0.5 to 30 pph N-vinylpyrrolidone and 0.01 to 2 pph of a crosslinking agent and from about 0.5 to 8 pph of a thickening agent comprising a N-vinylpyrrolidone/acrylic acid copolymer and a plasticizer comprising a polyhydric alcohol and the step of disposing the second layer comprises disposing on the first layer a monomeric mixture comprising from about 15 to 30 pph acrylic acid, 0.5 to 30 pph N-vinylpyrrolidone and 0.01 to 2 pph of a crosslinking agent and from about 0.5 to 8 pph of a thickening agent comprising a N-vinylpyrrolidone/acrylic acid copolymer and a plasticizer comprising a polyhydric alcohol.

4. The method according to claim 1 further comprising the step of disposing a scrim onto the partially cured first liquid before disposing the second layer.

5. The method according to claim 4 wherein the step of disposing the scrim includes selectively embedding at least a portion of the scrim into the partially cured first layer.

6. The method according to claim 1 further comprising the step of disposing a curable scrim layer onto the partially cured first liquid and curing the scrim layer before disposing the second layer.

7. The method according to claim 1 further comprising the steps of forming pockets in the partially cured first liquid and disposing physiologically active ions in the pockets before disposing the second layer.

8. The method according to claim 1 further comprising the step of disposing a layer including physiologically active ions onto the partially cured first liquid before disposing the second layer.

9. The method according to claim 8 further comprising the step of disposing a curable scrim layer onto the layer including physiologically active ions and curing the scrim layer before disposing the second layer.

10. The method according to claim 1 wherein the step of curing the first and second liquids includes the liquid with an ultraviolet source having a wavelength resonant with a photoinitiator in each of the liquids.

* * * * *